United States Patent
Shen et al.

(10) Patent No.: US 8,749,784 B1
(45) Date of Patent: Jun. 10, 2014

(54) PROBING CIRCUIT FEATURES IN SUB-32 NM SEMICONDUCTOR INTEGRATED CIRCUIT

(71) Applicant: CheckPoint Technologies, LLC., San Jose, CA (US)

(72) Inventors: Yaoming Shen, Santa Clara, CA (US); Guoqing Xiao, Saratoga, CA (US)

(73) Assignee: CheckPoint Technologies, LLC, San Jose, CA (US)

( * ) Notice: Subject to any disclaimer, the term of this patent is extended or adjusted under 35 U.S.C. 154(b) by 0 days.

(21) Appl. No.: 13/655,126

(22) Filed: Oct. 18, 2012

(51) Int. Cl.
*G01J 4/00* (2006.01)

(52) U.S. Cl.
USPC .......................................... 356/369; 356/364

(58) Field of Classification Search
CPC ............ G01N 21/9501; G01N 21/965; G01N 21/4738; G01N 21/21
USPC ........... 356/369, 364, 491, 492, 237.1–237.5, 356/239.3, 239.7, 239.8; 382/144, 151, 382/145; 324/537, 501, 724, 717–719
See application file for complete search history.

(56) References Cited

U.S. PATENT DOCUMENTS

| | | | |
|---|---|---|---|
| 7,224,828 B2 | 5/2007 | Cotton | |
| 7,643,137 B2 * | 1/2010 | Sugihara et al. | 356/237.2 |
| 7,659,981 B2 | 2/2010 | Lo | |
| 2004/0160604 A1 * | 8/2004 | Meeks et al. | 356/364 |
| 2010/0182602 A1 * | 7/2010 | Urano et al. | 356/369 |

* cited by examiner

Primary Examiner — Tri T Ton
(74) Attorney, Agent, or Firm — SV Patent Service

(57) ABSTRACT

A method for detecting ultra-fine features of an integrated circuit (IC) on a semiconductor substrate is disclosed. The semiconductor substrate comprises an IC fabricated by 22 nanometer or smaller scale semiconductor micro-fabrication process. The integrated circuit includes circuit features parallel to a circuit horizontal direction or a circuit vertical direction. The method includes focusing an incident light to produce a focused light spot on a portion of the IC. The incident light is linearly polarized in a linear polarization substantially parallel to the circuit horizontal direction. The method includes detecting reflected light from the portion of the IC, producing a relative movement between the focused light spot and the IC to allow the focused light to illuminate different portions of the IC, obtaining an image of the IC using signals of the reflected light detected from different locations of the integrated circuit, and detecting IC features in the image.

15 Claims, 8 Drawing Sheets

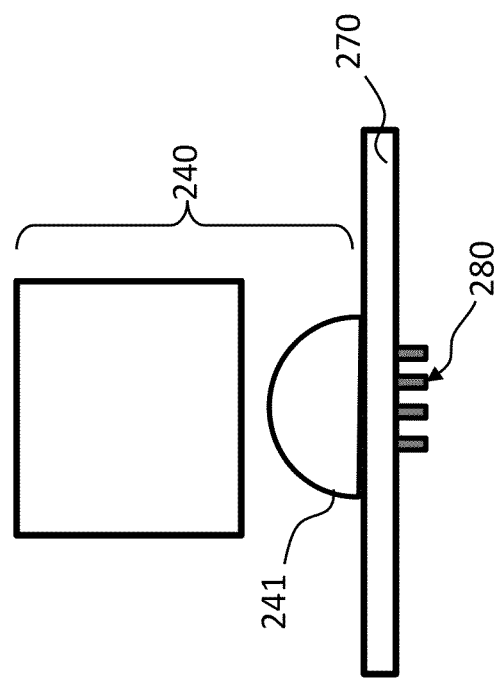

PROBING CIRCUIT FEATURES IN SUB-32 NM SEMICONDUCTOR INTEGRATED CIRCUIT

BACKGROUND OF THE INVENTION

The present application relates to system and method for probing ultra-fine features in integrated circuits (ICs), and in particular, to optical microscopy techniques for probing sub-32 nm semiconductor integrated circuits.

To improve an integrated circuit functionality and performance, IC manufacturers have been, in the last four decades, shrinking the sizes of circuit components and at the same time, increasing the number of circuit components. It becomes necessary to reduce the size of the circuit features, that is, as shown in FIG. 1, the lines and spaces that make up the circuit elements on the semiconductor substrate. The circuit features, referring to FIG. 1, are predominantly aligned along two orthogonal X and Y directions. One direction (e.g. x) can be called the circuit horizontal direction; another direction (e.g. y) can be called the circuit vertical direction. The minimum feature size that can be accurately produced on a substrate is limited by the ability of the fabrication process to form an undistorted optical image of the mask pattern onto the substrate, by the chemical and physical interaction of the photo-resist with the developer, and by the uniformity of the subsequent process (e.g., etching or diffusion) that uses the patterned photo-resist.

The minimum feature size of an IC is defined by design rules. Design Rules are a series of parameters provided by semiconductor manufacturers that enable the designer to verify the correctness of a mask set. Design rules are specific to a particular semiconductor manufacturing process. A design rule set specifies certain geometric and connectivity restrictions to ensure sufficient margins to account for variability in semiconductor manufacturing processes, so as to ensure that most of the parts work correctly. The most basic design rules are single layer rules. For example, a width rule specifies the minimum width of any shape in the design. A spacing rule specifies the minimum distance between two adjacent objects. The smallest rules, as defined by the International Technology Roadmap for Semiconductors (ITRS), have decreased from 65 nm in 2006, 45 nm in 2008, and 32 nm in 2010, to 22 nm in 2012 and 14 nm (~2014) for the current and next generation CMOS IC fabrication technologies.

As electronic devices become more miniaturized and more powerful, IC devices become smaller and more devices are packed in each chip. The cost of manufacturing has increased and the yield is decreased and the new causes of yield decrease emerge as new materials used and shrinking process variation tolerances.

Probing tools are frequently utilized during testing and debugging integrated circuit (IC) designs and layouts, where efforts are focused on defect localization and accurate waveform and timing measurements of signal switching inside sub-volt devices. Signal measurements are performed through the back side of the device.

The rapidly decreasing circuit features in electronic devices present significant challenge to debug and analytical tools to discern increasingly smaller circuit features and to preform timing analysis on a given transistor node.

Accordingly, there is a need for improved analytical method to probe and analyze ultra-fine circuit features in ICs fabricated by 22 nm or smaller CMOS technologies.

SUMMARY OF THE INVENTION

This present application discloses a novel microcopy method for testing and probing ultra-fine features in semiconductor integrated circuits fabricated sub-32 nm complementary metal-oxide-semiconductor (CMOS) processes. The disclosed system and method can probe or enhance small modulated signal which would otherwise not being detected on sub-32 nm integrated circuit.

In one general aspect, the present invention relates to a method for detecting ultra-fine features of an integrated circuit on a semiconductor substrate. The method includes positioning an optical focus system in vicinity of contact with a first planar surface of a semiconductor substrate, wherein the semiconductor substrate comprises an integrated circuit (IC) fabricated by 22 nanometer or smaller scale semiconductor micro-fabrication process, wherein the IC includes circuit features parallel to a circuit horizontal direction or a circuit vertical direction, wherein the circuit horizontal direction and circuit vertical direction are substantially parallel to the first planar surface; focusing a first incident light by the optical focus system to produce a first focused light spot on a portion of the integrated circuit in the semiconductor substrate, wherein the first incident light is linearly polarized in a first linear polarization substantially parallel to the circuit horizontal direction; detecting, by a photo detector, a first reflected light reflected from the portion of the integrated circuit in the semiconductor substrate; producing, by a scanning system, a relative movement between the first focused light spot and the integrated circuit to allow the first focused light to illuminate different portions of the integrated circuit; obtaining a first image of the integrated circuit using signals of the first reflected light detected from different locations of the integrated circuit; and detecting first features of the integrated circuit in the first image.

Implementations of the system may include one or more of the following. The first features of the integrated circuit in the first image include parallel linear circuit features substantially parallel to the circuit vertical direction. The parallel linear circuit features in the first image can be formed by a portion of the first reflected light that is diffracted by parallel circuit features in the IC. At least a portion of the first reflected light can be diffracted by the parallel circuit features in the IC. A half distance between identical adjacent features in the IC can be 22 nm or smaller. The semiconductor micro-fabrication process can include complementary metal-oxide-semiconductor (CMOS) process. The optical focus system can include a solid immersion lens, wherein the optical focus system comprises a tip in contact with the first planar surface of a semiconductor substrate, wherein the IC is constructed near a second planar surface of the substrate that is opposing to the first planar surface. The first incident light can be a laser beam. The first focused light spot can have a diameter of 240 nm or smaller. The method can further include blocking a low-spatial frequency portion of the first incident light before the first incident light is directed through the optical focus system, wherein the first reflected light is produced by a high-spatial frequency portion of the first incident light reflected by the IC in the semiconductor substrate. The method can further include rotating the first linear polarization of the first incident light by a polarization rotator to produce a second incident light having a second linear polarization substantially parallel to the circuit vertical direction; focusing the second incident light by the optical focus system to produce a second focused light spot on the first planar surface of the semiconductor substrate; detecting a second reflected light reflected from the semiconductor substrate by the photo detector; producing a relative movement between the second focused light spot and the integrated circuit by a scanning system; and obtaining a second image of the integrated circuit using signals of the second reflected light detected from different locations of the integrated circuit, wherein the first image comprises first features that do not exist in the second image. The first features of the integrated circuit in the first image can include parallel linear circuit features substantially parallel to the circuit vertical direction, wherein the parallel linear circuit features are not visible in the second image. The method can further include rotating the semiconductor substrate to align the circuit vertical direction substantially parallel to the first linear polarization of the first incident light; detecting a second reflected light reflected from the semiconductor substrate by the photo detector; producing a relative movement between the first focused light spot and the integrated circuit by a scanning system; and obtaining a second image of the integrated circuit using signals of the second reflected light detected from different locations of the integrated circuit, wherein the first image comprises first features that do not exist in the second image. The first features of the integrated circuit in the first image comprise parallel linear circuit features substantially parallel to the circuit vertical direction, wherein the parallel linear circuit features are not visible in the second image.

In another aspect, the present invention relates to a method for detecting ultra-fine features of an integrated circuit on a semiconductor substrate. The method includes positioning an optical focus system in vicinity of a first planar surface of a semiconductor substrate, wherein the semiconductor substrate comprises an integrated circuit (IC) fabricated by 22 nanometer or smaller scale semiconductor micro-fabrication process, wherein the IC includes circuit features parallel to a circuit horizontal direction or a circuit vertical direction, wherein the circuit horizontal direction and circuit vertical direction are substantially parallel to the first planar surface; inputting an oscillating signal into the integrated circuit, wherein the oscillating signal is modulated at a modulation frequency; focusing a first incident light by the optical focus system to produce a first focused light spot on a portion of the integrated circuit in the semiconductor substrate, wherein the first incident light is linearly polarized in a first linear polarization substantially parallel to the circuit horizontal direction; detecting, by a photo detector, a first reflected light reflected from the portion of the integrated circuit in the semiconductor substrate; and obtaining a first waveform from the first reflected light detected from the portion of the integrated circuit in the semiconductor substrate.

Implementations of the system may include one or more of the following. The photo detector detects the first reflected light while locking at the modulation frequency or half of the modulation frequency. The method can further include rotating the first linear polarization of the first incident light by a polarization rotator to produce a second incident light having a second linear polarization substantially parallel to the circuit vertical direction; focusing the second incident light by the optical focus system to produce a second focused light spot on the portion of the integrated circuit in the semiconductor substrate; detecting, by a photo detector, a second reflected light reflected from the portion of the integrated circuit in the semiconductor substrate; and obtaining a second waveform from the second reflected light detected from the portion of the integrated circuit in the semiconductor substrate, wherein the first waveform has an amplitude at least five times stronger than the second waveform. The method can further include rotating the semiconductor substrate to align the circuit vertical direction substantially parallel to the first linear polarization of the first incident light; detecting, by a photo detector, a second reflected light reflected from the portion of the integrated circuit in the semiconductor substrate; and obtaining a second waveform from the second reflected light detected from the portion of the integrated circuit in the semiconductor substrate, wherein the first waveform has an amplitude at least five times stronger than the second waveform. The optical focus system comprises a solid immersion lens, wherein the optical focus system comprises a tip. The method can further include bringing the tip in contact with the first planar surface of a semiconductor substrate.

These and other aspects, their implementations and other features are described in detail in the drawings, the description and the claims.

BRIEF DESCRIPTION OF THE DRAWINGS

FIG. 3 is a cross-sectional view of an implementation of the optical focus system in the integrated-circuit probing system and the semiconductor substrate comprising an integrated circuit shown in FIGS. 2A and 2B.

DETAILED DESCRIPTION OF THE INVENTION

Figure 1:
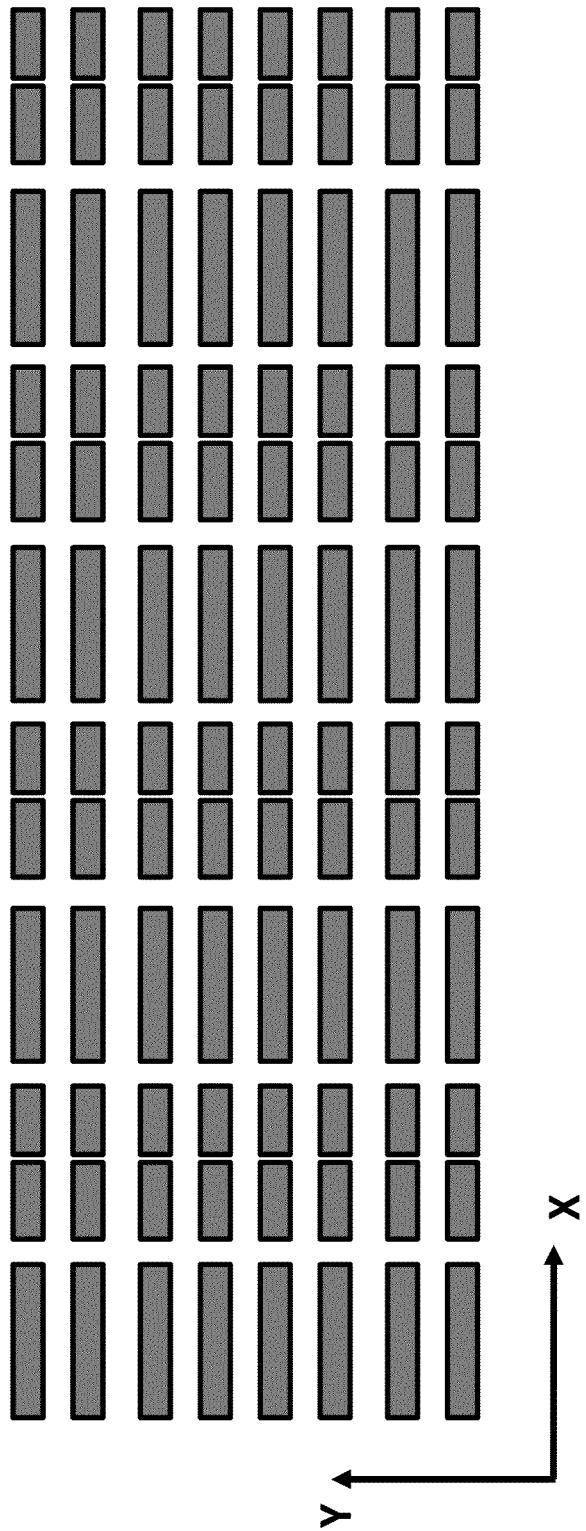
FIG. 1 is a schematic diagram showing exemplified features of an integrated circuit.
Figure 2A:
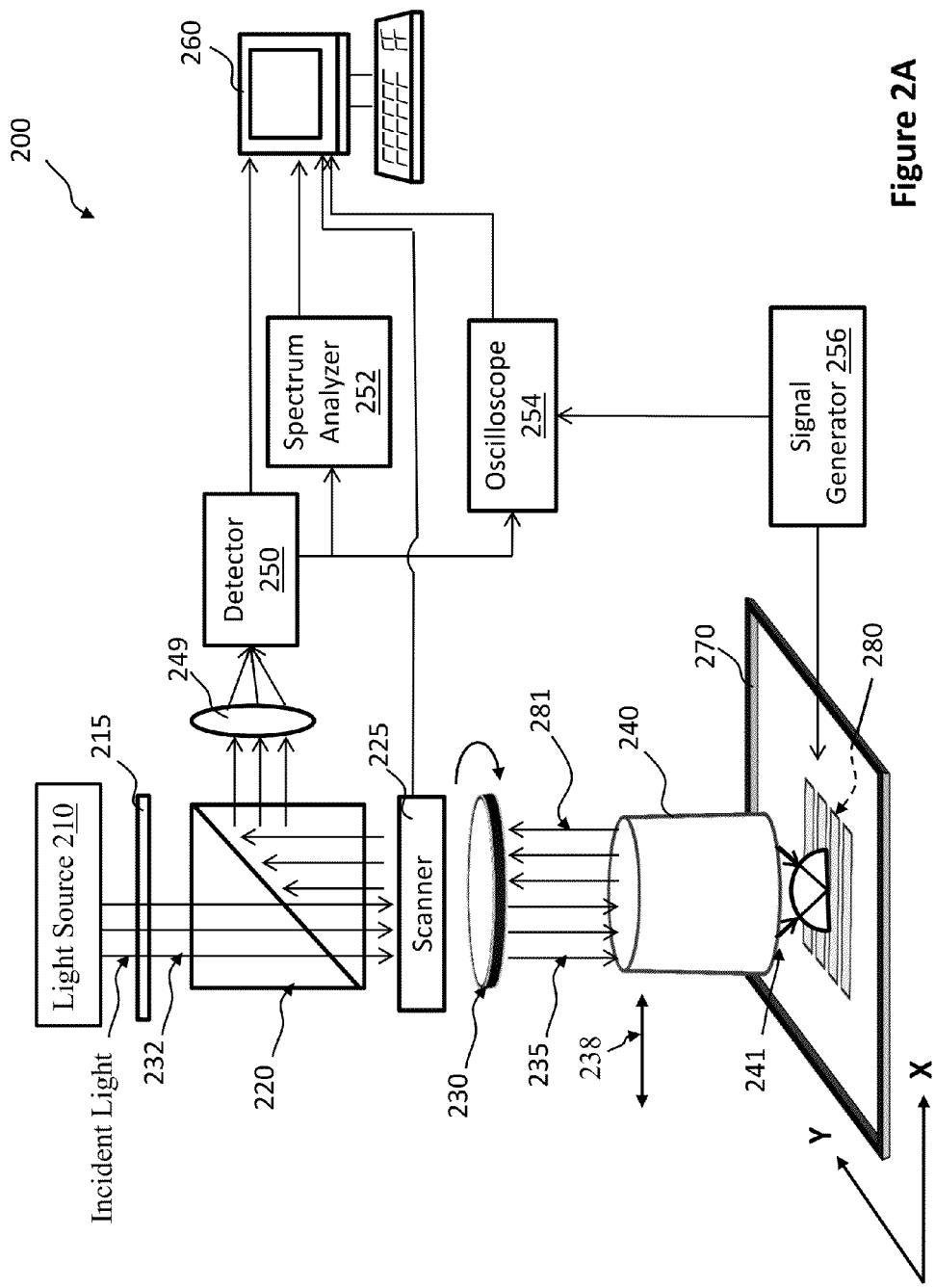
FIGS. 2A and 2B are schematic diagrams of integrated-circuit probing systems for probing features of an integrated circuit on a semiconductor substrate.
Figure 2B:
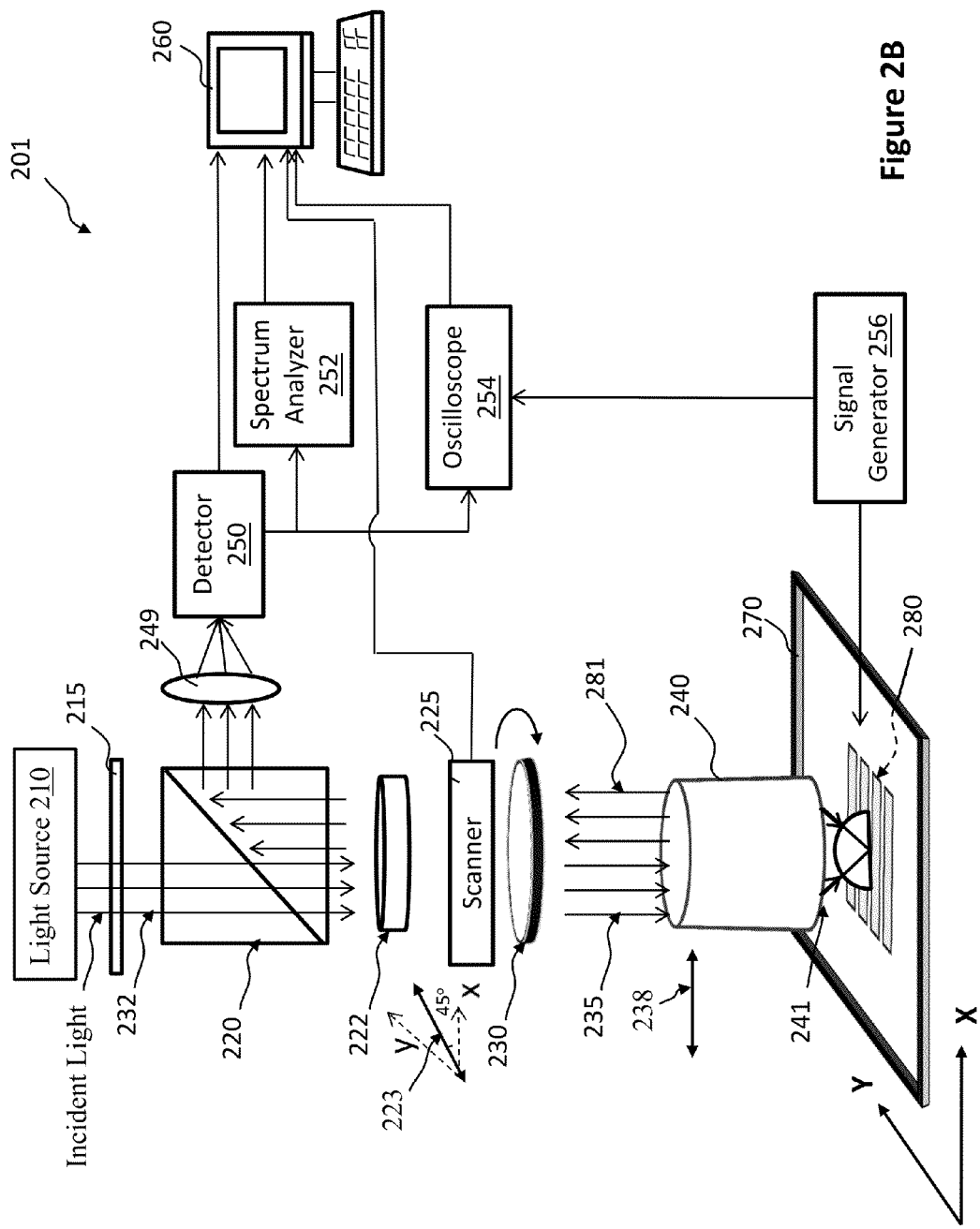

Referring to FIGS. 2A, 2B, and 3, an integrated-circuit probing system 200 includes a light source 210, a linear polarizer 215, a beam splitter 220, a scanning system 225, a polarization rotator 230, an optical focus system 240, a photo detector 250, a spectrum analyzer 252, an oscilloscope 254, a signal generator 256, and a computer 260. The light source 210 can be implemented by a laser emitting device (such as tunable or continuous wave (CW) laser source or other light sources such as a pulsed or mode-locked laser), or a non-coherent light source. Incident light emitted by the light source 210 passes through the linear polarizer 215, which produces a linearly polarized light. And then pass the beam splitter 220, then through the polarization rotator 230 which rotates the linearly polarized light 235 with polarization aligned in direction 238. The optical focus system 240 can be implemented by a solid immersion lens (SIL) assembly, as shown in FIG. 3. The photo detector 250 can be implemented by an avalanche photo detector. The scanning system 225 can be implemented by moveable galvo mirrors which can also include Acoustic-Optics Device, deflector scanning lens, and tube lens etc.

The incident light is polarized by the linear polarizer 215 to produce linearly polarized light 232. The polarization rotator 230 can be implemented by a half wave plate, which allows the incident light to pass through while keeping the same linear polarization. The half plate can be rotated by 45 degree to rotate the linear polarization of the incident light by 90 degrees. Linearly polarized light 235 through the polarization rotator 230 can have two linear polarization directions respectively aligned parallel to the circuit horizontal or circuit vertical directions.

The linearly polarized light 235 is directed to the optical focus system 240. The optical focus system 240 can include a family of lenses (not shown) and a SIL tip 241 (FIG. 3) that is pressed against a first (e.g. upper) planar surface of a semiconductor substrate 270. The semiconductor substrate 270 includes an integrated circuit 280 that is constructed on or near a second planar surface (the lower side opposing to the first planar surface) of the semiconductor substrate 270. The majority of circuit features in the integrated circuit 280 are aligned parallel to the x and y directions. As described below, the presently disclosed integrated-circuit probing system is particularly suitable for integrated circuit fabricated by CMOS processes with design rules at 32 nm or smaller. In one aspect, a design rule can be defined as a half distance between identical adjacent features in an integrated circuit. In other words, in a 22 nm IC, some identical adjacent features are defined by half distance that is 22 nm or smaller. In a 14 nm IC, some identical adjacent features are defined by half distance that is 14 nm or smaller.

The family of lenses (not shown) and the SIL tip 241 in the optical focus system 240 are configured to focus the linearly polarized light 235 at the integrated circuit 280. The optical focus system 240 has a high magnification and a high numerical aperture (N.A.) with a high-refractive-index solid material, which produces a laser spot of 240 nm or smaller at the IC 280. The reflected light 281 reflected by the integrated circuit 280 is predominantly polarized along the direction 238. The optical focus system 240 combines the advantages of conventional microscopy with those of near-field techniques. The high N. A. optical focus system 240 can form a tight focused laser spot at the integrated circuit 280 on the substrate as well as light collection, thus significantly improving collection efficiency.

The reflected light 281 passes the polarization rotator 230 that passes the majority of the reflected light 281 collected from the integrated circuit 280. The reflected light 281 is directed by the beam splitter 220 and focused by a lens 249 to the photo detector 250, wherein an image element of the integrated circuit 280 is formed.

The integrated-circuit probing system 200 can acquire images of the integrated circuit 280 by scanning a focused laser spot formed by an incident laser beam. The laser spot, having a width only a fraction of the dimension of the integrated circuit 280, is scanned across the x and y directions of the integrated circuit 280 by the scanning system 225 which comprise moveable mirrors that can steer a laser beam in two dimensions. The light reflected from different locations of the integrated circuit 280 forms an image element in the photo detector 250. The detected light signals from different locations of the integrated circuit 280 respectively represent image elements, which are combined by the computer 260 to form a laser scanning image of the integrated circuit 280.

It should be noted that the polarization direction (i.e. the direction 238) of the linearly polarized light 235 is parallel to one of the directions (x or y) for the circuit features in the integrated circuit 280. For example, the linear polarization direction of the linearly polarized light 235 is parallel to x axis, and so is the polarization direction of the vast majority portion of the reflected light 281.

After the image is produced, the polarization rotator 230 can be rotated to turn the polarization of the linearly polarized light by 90 degree such that the polarization is parallel to the y axis for the integrated circuit 280. Another image of the integrated circuit 280 is formed by the photo detector 250, which can be analyzed by the computer 260.

In some embodiments, an integrated-circuit probing system 201 is shown in FIG. 2B. The beam splitter 220 can be implemented by a Polarizing Cube beam splitter in combination with an additional Faraday rotator 222 positioned between the beam splitter 220 and the scanner 225. The Faraday rotator can rotate linearly polarized light by 45 degree as indicated by polarization direction 223. The half wave plate can either rotate the polarization direction 223 back to the original polarization (horizontal polarization) or rotate an additional 45 degree to the vertical polarization. The benefit of this setup is to allow the detector 250 to acquire close to full signal, significantly higher than the signal intensity acquired in integrated-circuit probing system 200.

In accordance with the present invention, it is discovered that linearly polarized light can pick up certain ultra-fine parallel circuit features that are either aligned perpendicular or parallel to the polarization of the incident light. The choice of the two alignment directions can depend on the material composition and distribution in the semiconductor substrate. This phenomenon is only visible in integrated circuits fabricated by CMOS technologies with design rules smaller than 32 nm (e.g. at 22 nm or smaller scale).

Figure 5:
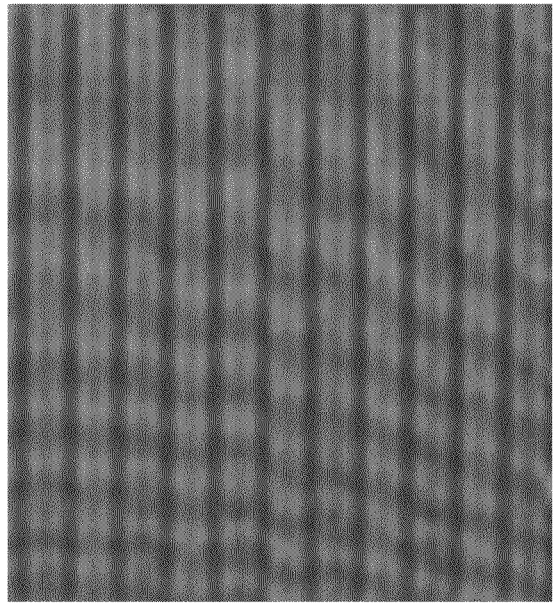
FIG. 5 is a laser scanning image obtained by the microscopy system in FIGS. 2A and 2B when the incident laser beam is linearly polarized along a circuit vertical direction.
Figure 4:
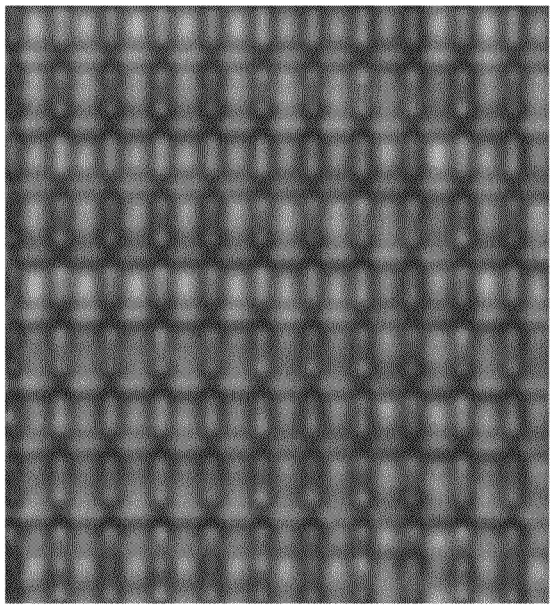
FIG. 4 is a laser scanning image obtained by the microscopy system in FIGS. 2A and 2B when the incident laser beam is linearly polarized along a circuit horizontal direction.
Figure 6:
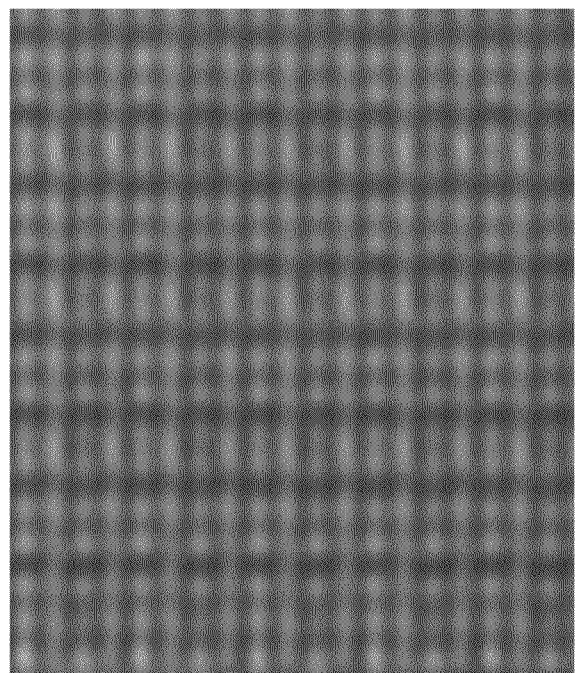
FIG. 6 is a laser scanning image obtained by the microscopy system in FIGS. 2A and 2B when the incident laser beam is circularly polarized.

Referring to FIG. 4, an image of a 22 nm integrated circuit is acquired by laser scanning with the linearly polarized light 235 linearly polarized in the X direction (i.e. circuit horizontal direction). In FIG. 5, another image is acquired by laser scanning from the same 22 nm integrated circuit with the linearly polarized light 235 linearly polarized in the Y direction (i.e. circuit vertical direction). By comparing FIGS. 4 and 5, it is clear that FIG. 4 reveals, at enhanced resolution and contrast, parallel linear circuit features aligned along the vertical direction, that is, perpendicular to the polarization of the incident light and most of the reflected light. FIG. 5, on the other hand, does not include such circuit vertical features. When the incident light is circularly polarized, the resulting image in FIG. 6 has features in between those in FIGS. 4 and 5.

The present inventors have confirmed this phenomenon at different focal depths, in single or multiple layers of different 22 nm integrated circuits. This effect is not significant on 32 nm circuit. It is postulated that as the circuit features become more densely packed, lights reflected by parallel circuit features can interfere with each other. In essence, parallel circuit features (with contrast in structures, material compositions, and depths, etc.) could act like a grating diffracting light away from integrated circuit. Such phenomenon become visible at 22 nm and smaller scale integrated circuits. The diffracted light by parallel circuit features can be used as a powerful signature for detecting circuit features and circuit defects, which could play a crucial role in the current and future generation IC manufacturing technologies.

In some embodiments, referring to FIG. 2A, the light source 210 in the integrated-circuit probing system 200 is implemented by a continuous-wave laser. The signal generator 256 generates and inputs an oscillating signal into the integrated circuit 280 at a modulation frequency. A typical modulation frequency is in the radio frequency range. The spectrum analyzer 252 receives at least a portion of the detect signal from the photo detector 250 and locks the signal at a data frequency which is the same or at half value of the modulation frequency. The output of the spectrum analyzer 252 varies as the focused laser spot moves to different locations of the integrated circuit 280, as shown in FIG. 4.

Figure 7:
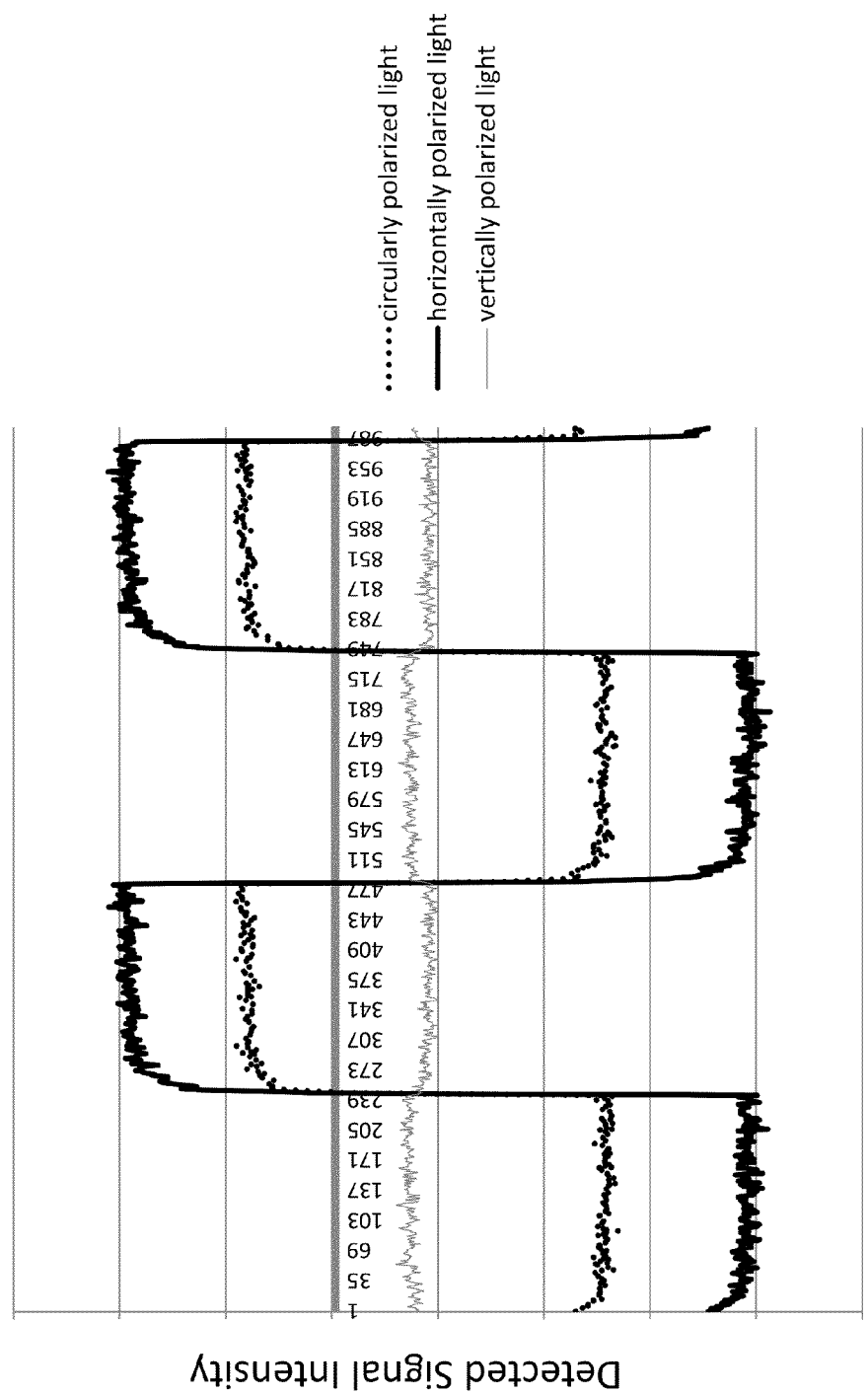
FIG. 7 shows waveforms of detected signals from modulated signals to the integrated circuit.

The scanner 225 is then fixed at a location on the integrated circuit 280 that produces high signal intensity. The signals from the photo detector 250 can be directed to the oscilloscope 254 to produce waveforms, as shown in FIG. 7. The waveforms in FIG. 7 are respectively produced by horizontally polarized light, vertically polarized light, and circularly polarized light (respectively corresponding to FIGS. 4, 5 and 6). The waveforms show that horizontally polarized light can produce signal intensity more than twice of circularly polarized light, and more than ten times of vertically polarized light at the same input laser power. The large signal strength allows the horizontally polarized light to detect circuit features not detectable by circularly polarized light or vertically polarized light.

It should be noted that the presently disclosed methods and systems are different from conventional techniques. Most conventional techniques use non-polarized incident laser beams. Some incident beams are modulated in amplitude. Some include reference light beams and detect interference between the reflected light the reference light beams. Another conventional technique divides the incident laser beam into two beams of mutually orthogonal polarizations: one beam simulating a reference beam and the other simulating a probing beam. Both the reference and probing beams are directed to the integrated circuit under test. The lights reflected from the two beams interfere with each other and are detected. In contrast, the presently disclosed system and method use a single incident light in one linear polarization direction without a reference light. The majority of reflected light that forms the detected image has substantially the same linear polarization as the incident light. In other words, the probing of the ultra-final circuit features in sub-32 nm integrated circuit in the present disclosure does not rely on (but does not need to exclude) cross-polarized reflective signals. When a linear polarizer is used, no cross polarized component in the reflected light is used for producing an image of the integrated circuit.

Figure 8:
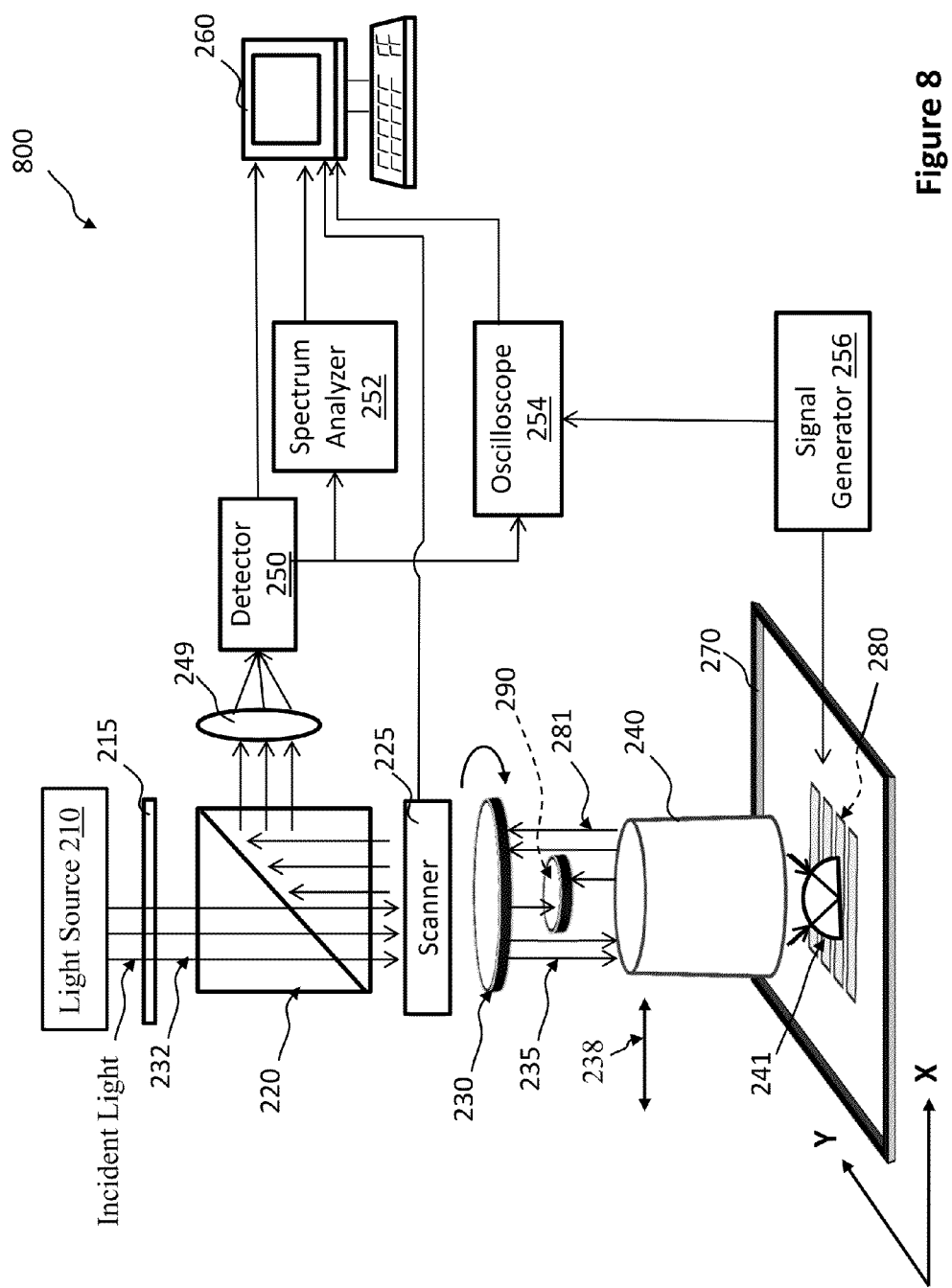
FIG. 8 is a schematic diagram of another microscopy system for probing features of an integrated circuit on a semiconductor substrate.

In some embodiments, referring to FIG. 8, an integrated-circuit probing system 800 can include similar components in the integrated-circuit probing system 200 as described above, and in addition, an obstruction plate 290 that is used to block the low spatial frequency components of the linearly polarized light 235 and the reflected light 281. The low spatial frequency light refers to the portion of light that has low- or zero-angle relative to the optical axis. By blocking low spatial frequency light components, the size of laser spot at the IC 280 is decreased. For example, the optical focus system 240 can have a N.A. of 0.87 or 0.95, which produces a laser spot narrower than 240 nm at the IC 280. As a result, image resolution can be further improved compared to the integrated-circuit probing system 200.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination.

Only a few examples and implementations are described. Other implementations, variations, modifications and enhancements to the described examples and implementations may be made without deviating from the spirit of the present invention. For example, the presently disclosed system and methods are not limited to 22 nm and 14 nm as described above, but are also suitable for integrated circuits fabricated by other design rules (currently defined or conventions to be defined in the future) at or smaller than 22 nm. Moreover, the linear polarization of the incident light and/or the reflected light can be accomplished by devices other than the examples described above.

It should also be noted that the polarized incident light and the reflected light are shown unsymmetrically relative to the axis of the solid immersion lens assembly in FIGS. 2A, 2B, and 8 for illustration purpose. The polarized incident light and the reflected light in general can be distributed around the axis of the solid immersion lens assembly in substantially cylindrical symmetric distribution.

Moreover, the scanning system can be implemented in different configurations to produce relative movements between the focused laser spot and the integrated circuit. For example, instead of directing the movement of the laser spot, the laser spot can be fixed and the scanning system can move the semiconductor substrate and thus the integrated circuit along x and the y directions.

Furthermore, the rotation of the linear polarization of the light beam impinging the integrated circuit can be achieved by different configurations. Instead of rotating the linear polarization of the incident light by a polarization rotator, as described above, the polarization of the incident light can be fixed; the semiconductor substrate and thus the integrated circuit can be rotated by a rotation mechanism by 90 degrees align the linear polarization of the incident light in the circuit horizontal direction or the circuit vertical direction.

What is claimed is:

1. A method for detecting ultra-fine features of an integrated circuit on a semiconductor substrate, comprising:
    positioning an optical focus system in vicinity of a first planar surface of a semiconductor substrate, wherein the semiconductor substrate comprises an integrated circuit (IC) fabricated by 22 nanometer or smaller scale semiconductor micro-fabrication process, wherein the IC includes circuit features parallel to a circuit horizontal direction or a circuit vertical direction, wherein the circuit horizontal direction and the circuit vertical direction are substantially parallel to the first planar surface;
    inputting an oscillating signal into the integrated circuit;
    focusing a first incident light by the optical focus system to produce a first focused light spot on a portion of the integrated circuit in the semiconductor substrate, wherein the first incident light is linearly polarized in a first linear polarization substantially parallel to the circuit horizontal direction;
    detecting, by a photo detector, a first reflected light reflected from the portion of the integrated circuit in the semiconductor substrate;
    obtaining a first waveform from the first reflected light detected from the portion of the integrated circuit in the semiconductor substrate;
    rotating the first linear polarization of the first incident light by a polarization rotator to produce a second incident light having a second linear polarization substantially parallel to the circuit vertical direction;
    focusing the second incident light by the optical focus system to produce a second focused light spot on the portion of the integrated circuit in the semiconductor substrate;

detecting, by the photo detector, a second reflected light reflected from the portion of the integrated circuit in the semiconductor substrate; and obtaining a second waveform from the second reflected light detected from the portion of the integrated circuit in the semiconductor substrate.

2. The method of claim 1, wherein the oscillating signal is modulated at a modulation frequency, wherein the photo detector detects the first reflected light while locking at the modulation frequency or half of the modulation frequency.

3. The method of claim 1, wherein the first reflected light reflected from the portion of the integrated circuit in the semiconductor substrate passes through the polarization rotator before being detected by the photo detector.

4. The method of claim 1, wherein the polarization rotator is a half wave plate.

5. The method of claim 4, further comprising:
rotating the first linear polarization of the first incident light by 45 degrees by a Faraday rotator before the step of rotating the first linear polarization of the first incident light by a polarization rotator.

6. The method of claim 5, wherein the second reflected light reflected from the portion of the integrated circuit in the semiconductor substrate passes through the half wave plate and the Faraday rotator before being detected by the photo detector.

7. The method of claim 1, wherein the amplitude of the first waveform is stronger than the second waveform.

8. The method of claim 7, wherein the amplitude of the first waveform is at least five times stronger than the second waveform.

9. The method of claim 1, wherein the oscillating signal is modulated at a modulation frequency.

10. The method of claim 1, wherein the optical focus system comprises a solid immersion lens, wherein the optical focus system comprises a tip, the method further comprising:
bringing the tip in contact with the first planar surface of a semiconductor substrate to focus the first incident light on the portion of the integrated circuit in the semiconductor substrate.

11. The method of claim 1, wherein at least a portion of the first reflected light is diffracted by the circuit features parallel to the circuit horizontal direction or the circuit vertical direction in the IC.

12. The method of claim 1, wherein a half distance between adjacent features in the IC is 22 nm or smaller.

13. The method of claim 1, wherein the semiconductor micro-fabrication process comprises complementary metal-oxide-semiconductor (CMOS) process.

14. The method of claim 1, wherein the first incident light is a laser beam.

15. The method of claim 1, wherein the first focused light spot has a diameter of 240 nm or smaller.

* * * * *